(12) United States Patent
Summer et al.

(10) Patent No.: US 9,650,272 B2
(45) Date of Patent: *May 16, 2017

(54) PREVENTION AND REMEDIATION OF PETROLEUM RESERVOIR SOURING AND CORROSION BY TREATMENT WITH VIRULENT BACTERIOPHAGE

(71) Applicant: Dow Global Technologies LLC, Midland, MI (US)

(72) Inventors: Elizabeth J. Summer, College Station, TX (US); Mei Liu, College Station, TX (US); Neil S. Summer, College Station, TX (US); Douglas Baldwin, College Station, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 218 days.

This patent is subject to a terminal disclaimer.

(21) Appl. No.: 14/060,297

(22) Filed: Oct. 22, 2013

(65) Prior Publication Data

US 2014/0061123 A1 Mar. 6, 2014

Related U.S. Application Data

(60) Continuation-in-part of application No. 13/396,444, filed on Feb. 24, 2012, now Pat. No. 8,585,899, which
(Continued)

(51) Int. Cl.
*C02F 1/02* (2006.01)
*C02F 3/00* (2006.01)
(Continued)

(52) U.S. Cl.
CPC .............. *C02F 3/34* (2013.01); *C02F 1/50* (2013.01); *C12N 2795/00031* (2013.01)

(58) Field of Classification Search
None
See application file for complete search history.

(56) References Cited

U.S. PATENT DOCUMENTS

| 3,105,014 A | 9/1963 | Harrison |
| 4,442,895 A | 4/1984 | Lagus et al. |

(Continued)

FOREIGN PATENT DOCUMENTS

| GB | WO 02/40642 A1 * | 5/2002 |
| JP | 02099196 | 4/1990 |

(Continued)

OTHER PUBLICATIONS

Fortier and Sekulovic, Importance of prophages to evolution and virulence of bacterial pathogens. Virulence, 2013; 4(5): 1-12.*
(Continued)

*Primary Examiner* — Janet L Andres
*Assistant Examiner* — Stuart W Snyder
(74) *Attorney, Agent, or Firm* — Tifani M. Edwards; Mary E. Bak

(57) ABSTRACT

There is provided a safe, natural, environmentally sound means of controlling bacterial contamination, corrosion, and souring of oil and gas wells and reservoirs that result from bacteria-contaminated water in a well. In one aspect it is a process for remediation of souring of petroleum reservoirs and coalbeds by adding to the water used in flooding and "fracing" operations an effective amount of virulent (non-lysogenic) bacteriophages (phages) specific for problematic target bacteria. The invention also provides a means for combating loss of effectiveness of bacterial control by staging bacteriophage production and application to control dominant and sub-dominant target bacteria in a community of target bacteria.

7 Claims, 3 Drawing Sheets

Related U.S. Application Data is a division of application No. 12/983,136, filed on Dec. 31, 2010, now Pat. No. 8,168,419.

(51) Int. Cl.
*C12Q 1/70* (2006.01)
*C09K 8/68* (2006.01)
*C02F 3/34* (2006.01)
*C02F 1/50* (2006.01)

(56) References Cited

U.S. PATENT DOCUMENTS

| | | | |
|---|---|---|---|
| 4,778,653 | A | 10/1988 | Kamimura et al. |
| 5,160,433 | A | 11/1992 | Niesen |
| 5,441,873 | A | 8/1995 | Knight et al. |
| 6,699,701 | B1 | 3/2004 | Sulakvelidze et al. |
| 6,926,833 | B2 | 8/2005 | Van Reis et al. |
| 7,256,160 | B2 | 8/2007 | Crews et al. |
| 7,674,467 | B2 | 3/2010 | Sulakvelidze |
| 7,882,895 | B2 | 2/2011 | Kabishcher et al. |
| 8,168,419 | B2 | 5/2012 | Baldwin et al. |
| 8,241,498 | B2 | 8/2012 | Summer et al. |
| 8,241,499 | B2 | 8/2012 | Liu et al. |
| 8,252,519 | B2 | 8/2012 | Baldwin et al. |
| 8,252,576 | B2 | 8/2012 | Campbell et al. |
| 8,585,899 | B2 | 11/2013 | Baldwin et al. |
| 2006/0094076 | A1 | 5/2006 | Stave et al. |
| 2008/0213752 | A1 | 9/2008 | Stave et al. |
| 2009/0104157 | A1 | 4/2009 | Solomon et al. |
| 2009/0180992 | A1* | 7/2009 | Summer et al. ............. 424/93.6 |
| 2009/0246336 | A1 | 10/2009 | Burnett et al. |
| 2011/0053144 | A1 | 3/2011 | Garcia Aljaro et al. |
| 2011/0281329 | A1 | 11/2011 | Lenherr et al. |
| 2013/0149753 | A1 | 6/2013 | Summer et al. |
| 2013/0149759 | A1 | 6/2013 | Summer et al. |
| 2014/0061123 | A1 | 3/2014 | Summer et al. |
| 2014/0102975 | A1 | 4/2014 | Summer et al. |

FOREIGN PATENT DOCUMENTS

| | | |
|---|---|---|
| WO | WO-2006/094076 | 11/2006 |
| WO | WO-2008/078978 | 7/2008 |

OTHER PUBLICATIONS

Abedon, S. et al. Experimental Examination of Bacteriophage Latent-Period Evolution as a Response to Bacterial Availability, Applied and Environmental Microbiology, Dec. 2003, 69 (12): 7499-7506.

Lu, T.K. et al., Dispersing biofilms with engineered enzymatic bacteriophage, PNAS, Jul. 2007, 104 (27): 11197-11202.

Zacheous, O.M. et al., Soft deposits, the key site for microbial growth in drinking water distribution networks, Water Research, May 2001, 35 (7): 1757-1765.

Scholtens, et al., ("Phage Typing of *Salmonella typhi* in the Netherlands", from the Rijks Instituut voor de Volksgezondheid, Utrecht; Jun. 6, 1950).

Greenberg, et al., ("Tracing Typhoid Carriers by Means of Sewage", presented at the 1957 annual meeting, California Sewage and Industrial Wastes Assn.; San Diego, CA.; May 1-4, 1957).

Derwent Translation of Araki et al. (JP 02099196) of Apr. 1990.

Sakaguchi, et al., (Control of Microbiofouling Using Bacteriophage 2. Detection of Phages and Fundamental Study of their Lytic Effect on Fouling Bacteria (Abstract Only), De.

Lee, et al., (Molecular analysis of a mixed-species biofilm on carbon steel. Abstracts of the General Meeting of the American Society for Microbiology. 2003; vol. 103:Q-156.

Jiang, S.C. et al., Significance of lysogeny in the marine environment: studies with isolates and a model of lysogenic phage production, Microbial Ecology, May 1998, 35 (3): 235-243.

McNair, et al., (Predicting Phage Preferences: Lytic vs. Lysogenic Lifestyle from Genomes:. 2013 from the San Diego State University).

Office Action dated Jun. 17, 2013 in related U.S. Appl. No. 13/465,700, filed May 7, 2012.

Applicant's Response dated Jul. 16, 2013 to the Office Action in related U.S. Appl. No. 13/465,700, filed May 7, 2012.

Office Action dated Nov. 5, 2013 in related U.S. Appl. No. 13/465,700, filed May 7, 2012.

Applicant's Response dated Dec. 18, 2013 to the Office Action in related U.S. Appl. No. 13/465,700, filed May 7, 2012.

Office Action dated Sep. 23, 2014 in related U.S. Appl. No. 13/465,700, filed May 7, 2012.

Applicant's Response dated Apr. 3, 2015 to the Office Action in related U.S. Appl. No. 13/465,700, filed May 7, 2012.

Office Action dated Aug. 5, 2015 in related U.S. Appl. No. 13/465,700, filed May 7, 2012.

Applicant's Response dated Nov. 5, 2015 to the Office Action in related U.S. Appl. No. 13/465,700, filed May 7, 2012.

Office Action dated Mar. 20, 2015 in related U.S. Appl. No. 14/056,808, filed Oct. 17, 2013.

Applicant's Response dated Apr. 3, 2015 to the Office Action in related U.S. Appl. No. 14/056,808, filed Oct. 17, 2013.

Office Action dated Apr. 23, 2015 in related U.S. Appl. No. 14/056,808, filed Oct. 17, 2013.

Applicant's Response dated Oct. 23, 2015 to the Office Action in related U.S. Appl. No. 14/056,808, filed Oct. 17, 2013.

Office Action dated Dec. 1, 2015 in related U.S. Appl. No. 14/056,808, filed Oct. 17, 2013.

Applicant's Response dated Apr. 29, 2016 to the Office Action in related U.S. Appl. No. 14/056,808, filed Oct. 17, 2013.

Office Action dated May 19, 2015 in related U.S. Appl. No. 14/133,115, filed Dec. 18, 2013.

Applicant's Response dated Oct. 19, 2015 in related U.S. Appl. No. 14/133,115, filed Dec. 18, 2013.

Office Action dated Jan. 29, 2016 in related U.S. Appl. No. 14/133,115, filed Dec. 18, 2013.

* cited by examiner

PREVENTION AND REMEDIATION OF PETROLEUM RESERVOIR SOURING AND CORROSION BY TREATMENT WITH VIRULENT BACTERIOPHAGE

RELATIONSHIP TO OTHER APPLICATIONS

This application is Continuation-In-Part application of and claims benefit of U.S. application Ser. No. 13/396,444, filed Feb. 24, 2012, and divisional U.S. application Ser. No. 12/983,136 filed Dec. 31, 2010 and claims benefit of Application Ser. No. 61/295,142 filed Jan. 14, 2010 and Application Ser. No. 61/783,415, filed Mar. 14, 2013 and application Ser. No. 14/056,808, filed Oct. 17, 2013. The disclosures of each of these applications are incorporated herein by reference in their entirety for all purposes.

FIELD OF THE INVENTION

This invention relates to remediation of souring (hydrogen sulfide production) and corrosion in oil and gas reservoirs caused by bacteria. More specifically, it relates to control of bacteria that produce acid and/or sulfur compounds that cause reservoir souring and corrosion; control being effected by reduction of targeted bacteria, particularly sulfate reducing bacteria (SRB) and acid producing bacteria (APB), with naturally occurring bacteriophage that are virulent for targeted bacteria and

BACKGROUND

Microorganisms, including bacteria, are ubiquitous in nature and can have profound negative effects on oil and natural gas recovery. Bacterial fouling of the water needed to hydrofracture ("frac") reservoir rock or to "water-flood," to increase production of oil and gas, can contaminate or "sour" the reservoir by producing hydrogen sulfide ($H_2S$). This decreases the value of the product and can make marginal wells unprofitable. Sulfate reducing bacteria (SRB) produce toxic, flammable $H_2S$, which shortens the lifetime and lowers the reliability of any piping and tankage, and introduces additional safety risks from drill rig to refinery. Acid producing bacteria (APB) produce acids, including sulfuric acid, which lead to additional corrosion.

Bacterial fouling leads to serious problems in the oil and gas industry. Bacterially-evolved hydrogen sulfide sours petroleum reservoirs, elevating risk and devaluing the product, while bacterial production of iron sulfide creates black powder accumulation, causing pipeline blockages. Microbially-influenced corrosion attacks the whole system, from fracture tank to refinery, and degrades fracture fluid additives.

In Barnett Shale operations in Texas, water is typically stored in large ponds which are open to the atmosphere prior to the start of fracturing work, allowing the water to become heavily contaminated with bacteria. In addition, bacteria become established in biofilms near the wellbore during shut-in of the well.

The Barnett Shale formation's low permeability requires the use of large-volume hydraulic fracturing technologies to enhance gas production. Other shale formations, such as the Marcellus in the eastern U.S., also require hydraulic fracturing. In a typical "frac" operation, water is collected in portable tanks or large, purpose-dug ponds from a variety of sources, including water wells pumping from aquifers, chlorinated city water supplies, and ponds, rivers, and lakes. Each of these water sources has some level of innate indigenous bacterial contamination that continues growing during the collection reservoirs' exposure to the atmosphere.

Hydrofracturing ("fracing") and "water flooding" is heavily dependent on the availability of water, and a typical horizontal "frac" operation requires one to five million gallons of water. The water is pumped into a production well at very high rates (one to over two hundred gallons per minute (gpm). Droughts such as that affecting the Barnett shale operational area have been common over the past several years. During times of drought, water recovered from previous hydro-fracture operations ("flow-back" or "produced" water) is reused, and mixed with "fresh" water in holding ponds or tanks. This reused water introduces elevated bacterial fouling concentrations and solids loadings. Even in times when no drought exists, the universal use of flow-back water in all "frac" operations is utilized to mitigate the expense and environmental harm done in removing and disposing the highly contaminated waste water and is increasingly being required by regulation.

To counter bacterial fouling and reservoir souring, chemical biocides, commonly hypochlorite bleach, are applied to the fracture water. The cost of the biocide treatment for a single typical "frac" operation can be as much as $50,000. Additionally, the design of recovery systems with sour service alloys, thicker pipe, and heavier valves leads to increases in capital expense.

The scale of the problem is enormous. The Barnett Shale underground natural gas formation extends over 5,000 square miles in north central Texas. A total of 6,519 gas wells with a further 4,051 permitted locations existed as of Aug. 15, 2007. Wells are being drilled within populated areas, such as the Dallas-Fort Worth city limits, where it is vital to minimize risk and environmental impact. The petroleum industry currently spends $2 billion on biocides annually. Broad spectrum biocides require the additional expenditures associated with regulatory compliance. These biocides may remain in the water when it is pumped out of the well, creating waste handling and disposal problems. Understandably, biocide usage in the petroleum industry is facing growing regulatory resistance because of the negative impact on the environment and associated health risks.

As well as requiring enormous expenditures, biocides are not sufficiently effective. Any bacteria that are endemic or are introduced into the formation encounter favorable growth temperatures and conditions during the "frac" and flooding operations, as the large volumes of water pumped downhole result in near wellbore cooling. Wells may be shut in following the operation while surface processing equipment and flowlines are installed, leaving time for bacteria to colonize. Once bacteria become established in a well, they develop biofilms that supply a stream of bacterial contamination downstream the well through water tanks, flow lines and disposal facilities. Biofilms protect the bacteria from the chemical biocides and a program of regular, high volume biocide application must be initiated merely to keep the free-swimming bacteria in check and minimize problem bacterial byproducts. Biofilms themselves are impervious to biocides, and can only be mechanically scoured, as with pipeline "pigs". In addition, there is increasing biocide resistance being observed in hydro-fracture and flood water bacteria.

Other reservoirs are "flooded" with water to enhance recovery—usually oil recovery. In "water flood" operations, injection wells are drilled into the producing horizon and water is pumped—as in fracturing—to displace the oil and/or gas through a formation into other "recovery" well(s) in the same field. Since the water is injected into the reservoir is contaminated with bacteria, similarly to the water used for "fracing," the same problems of souring, fouling, and corrosion occur.

Bacteria also cause a host of additional problems in other sectors of the petroleum industry. Another potential "expense" is the social cost of catastrophic failure. Microbiologically-induced corrosion (MIC) has been a factor in several major oil and gas pipeline incidents, including the well-publicized 2006 Alaska Pipeline spill. MIC occurs on the insides of pipes or storage vessels, and especially under biofilms.

A better control strategy would be: inexpensively manufactured, environmentally benign, adaptable to changing microorganisms to prevent resistance, targeted towards those microorganisms that constitute the threat, and capable of penetrating and destroying biofilms. Such a control strategy would optionally be able to sense and adjust to the different concentrations of microorganisms encountered, even within the well. The present invention is just such a strategy, providing bacterial control based on bacteriophages, the natural predators of bacteria.

SUMMARY OF THE INVENTION

The present invention is a safe, natural, environmentally sound means of controlling bacterial contamination, corrosion, and souring of oil and gas wells and reservoirs that result from bacteria-contaminated water in a well. More specifically, in one embodiment, the invention is a process for remediation of souring of petroleum reservoirs and coalbeds comprising: adding to the water used in flooding and "fracing" operations an effective amount of virulent (non-lysogenic) bacteriophages (phages) specific for APB and/or SRB. These phages may be produced by concentrating an aqueous solution of virulent bacteriophages from bacteria indigenous to the water. In another embodiment, the invention is a process for replication of bacteriophages comprising: a vessel with an inlet for an aqueous solution containing target bacteria; an inlet for an aqueous solution of bacteriophages virulent for target bacteria; an outlet for a solution containing replicated bacteriophage; wherein the flow rate of the inlet solution containing target bacteria and the flow rate for the solution containing bacteriophages virulent for target bacteria are adjusted to obtain substantially complete destruction of the target bacteria.

In yet another embodiment the invention provides a means for combating loss of effectiveness of bacterial control by staging bacteriophage production and application to control dominant and sub-dominant target bacteria in a community of target bacteria. Other more specific embodiments are disclosed in the Detailed Description of the Invention. The phage-based bacterial control technology of this invention will improve operational efficiencies and prolong the operational life of marginal wells that would ordinarily have been withdrawn from service. It will also decrease the capital costs of creating new wells by maintaining sweet gas production, mitigating the need for sour service pipes and hydrogen sulfide removal apparatus. The ability to recycle flowback water will decrease the cost and environmental impact of "frac" and flooding operations. An ancillary benefit will be the improvement of results from "frac" and flooding operations.

DESCRIPTION OF THE DRAWINGS

The accompanying Figures illustrate specific results from embodiments of the invention and, together with the general description of the invention given above, and the detailed description of the specific embodiments, serve to explain the principles of the invention.

DETAILED DESCRIPTION OF THE INVENTION

Figure 1:
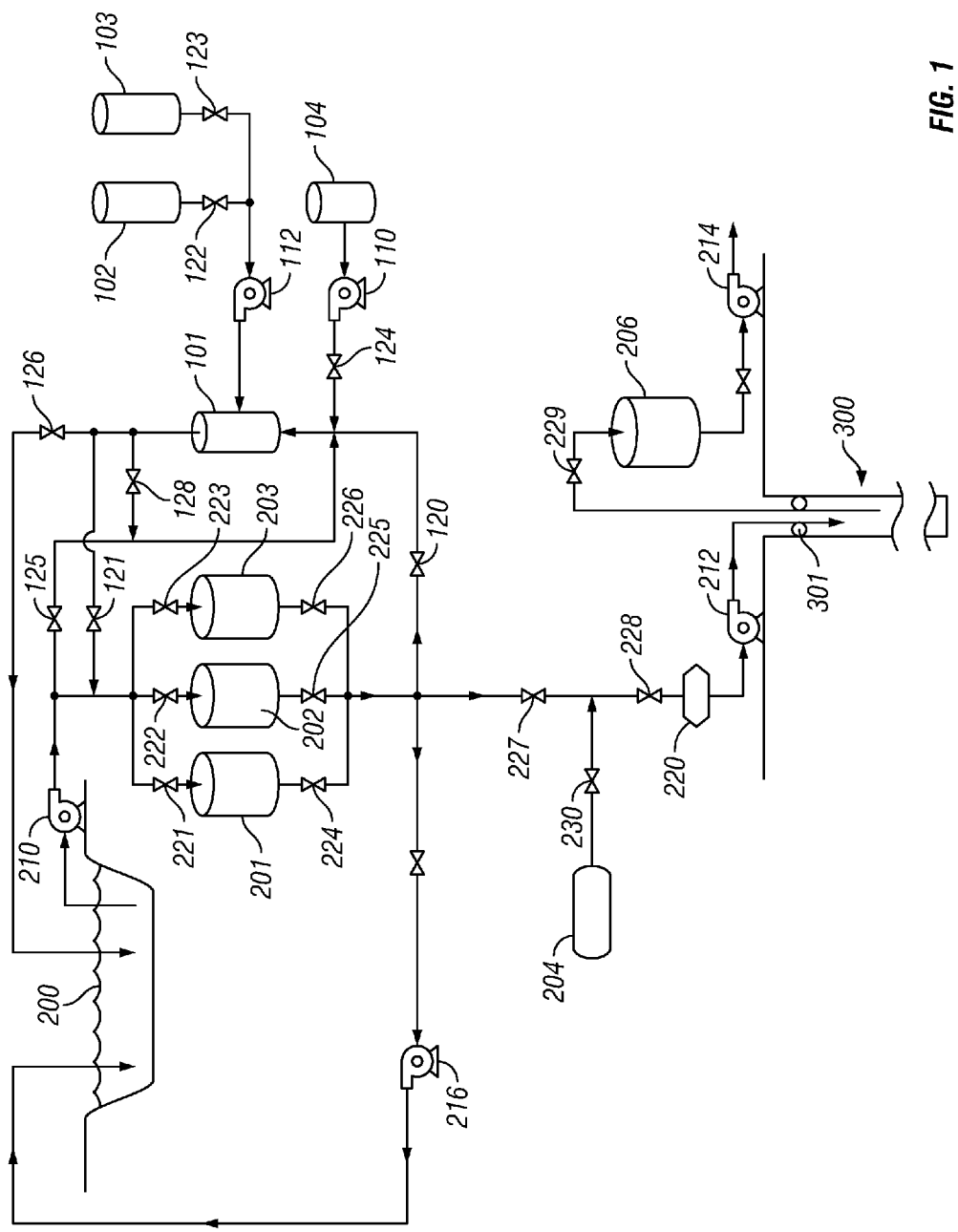
FIG. 1 is a diagrammatic representation of a process embodiment of the invention.

Current methods of microbial control in oil and gas geological formations and wells apply broad spectrum biocides, typically by injection into the stream of fracture or flood water at a blender prior to injection into the well. Customary biocides include glutaraldehyde, glutaraldehyde/quaternary ammonium compound blends, isothiazolin, tetrakis(hydromethyl) phosphonium sulfate (THPS), 2,2-dibromo-3-nitrilopropionamide, and bronopol. However, these biocides often have major health risks to humans and all animals in the food chain. THPS and hypochlorite bleach are the most commonly used antimicrobials in the Barnett shale operations area. These EPA registered biocides cannot be introduced into an open pond, as they will permeate into the groundwater, killing aquatic organisms and frequently being consumed by terrestrial animals. All biocides in use by the industry are intentionally employed in a broad spectrum manner. Their effectiveness is determined by conventional culturing methods which merely determine the presence of bacteria and make no attempt to determine genus or species. These methods are labor and material intensive and are essentially unchanged in the past forty years. In typical biocide assessment practices, samples of "frac" water are diluted and cultured in specialized growth medium under various conditions, with and without biocide, for various lengths of time and then compared for bacterial cell density, resulting in more than 40 test cultures each time. There are seasonal variations in bacteria, requiring different growth and test conditions, to which the bacteria may respond differentially. The results take days and, thus, cannot be used for rapid .optimization of biocide application. "Water scarcity leads to the reuse of hydrofracture water but when hydrofracture ponds are filled with this already bacterially-contaminated water at the last minute, the assays cannot return results on bacterial activity prior to the water being pumped into the well. The typical field solution to this uncertainty is to apply massively excessive concentrations of sodium hypochlorite. A useful alternative to this would be the instantaneous, on-line determination of bacterial concentrations directing the biocide administration." (*Use of Microbiocides in Barnett Shale Gas Well Fracturing Fluids to Control Bacteria Related Problems*; J. K. Fisher, K. Johnson, K. French and R. Oden, Paper 08658, NACE, International; 2008 Corrosion Conference and Expo.)

The present invention, in one embodiment, is a process of controlling the problem bacteria by using virulent bacteriophage, instead of synthetic biocides. Bacteriophages (bacteriophage and phage are terms that are used interchangeably herein and in the claims) are the ubiquitous and natural viruses which infect, are reproduced within, and lyse bacteria. Lytic phage infection is initiated when the tail proteins recognize and adsorb to specific cell surface features of the target bacterial host. This triggers the injection of the phage DNA into the bacterial cytoplasm. The genes in that DNA are expressed by the bacterium's own protein synthesis apparatus, resulting in the synthesis and assembly of approximately 30 to 100 progeny phage particles over the course of minutes to several hours. After, typically, 15 to 60 minutes, the cell explodes ("lysis") as a result of phage-encoded lytic enzymes, liberating hundreds of progeny phage that can then adsorb to new bacterial hosts and repeat the process. In this manner, bacteriophages replicate themselves. Random environmental samples indicate the presence of 10-100 phages for every bacterial cell, indicating $10^{30}$-$10^{31}$ phages in the biosphere.

There are important consequences to this life cycle. First, given a growing bacterial culture to attack, phages can proliferate at unimaginable rates. Within two hours of the addition of a single particle of the classical phage T7 to a laboratory culture of 10 billion *Escherichia coli* cells, more than 99.9% of the bacteria are destroyed and 10 trillion virus particles are generated. There is, thus, a scientific basis for calling bacteriophages "the only medicine that grows" and, in fact, many of the early myths of curative springs or rivers were grounded in the reality that phages existed in these waters at concentrations capable of curing leprosy or cholera (Hankin, 1896). Second, phages are specific for target (or matching) bacteria, because they generally only bind to the type of bacterium that their adsorption device, or "tail", recognizes, and that is encoded in their DNA. Thus, phages are harmless to other bacteria and, obviously, to higher organisms.

Phages do not infect plants or animals and are, therefore, safe to produce, store, handle and apply. Bacteriophages have been declared "Generally Recognized as Safe" for use in human food.

Because bacteriophages reproduce along with the microorganisms that they infect, in the method of this invention, once down-well, they will spread to other bacteria of the same species.

Virulent phages as the terms is used in this specification and claims means non-lysogenic phage—bacteriophage that infect bacteria produce a lytic cycle of replication. Virulent bacteriophage differs from temperate bacteriophage in the way in which they replicate and in DNA makeup. The following definitions from the Meyer, Microbiology and Immunology On-Line, Chapter Seven, Bacteriophage; University of South Carolina School of Medicine; http://pathmicro.med.sc.edu/mayer/phage.htm: "Lytic or virulent phages are phages which can only multiply on bacteria and kill the cell by lysis at the end of the life cycle." and "Lysogenic or temperate phages are those that can either multiply via the lytic cycle or enter a quiescent state in the cell. In this quiescent state most of the phage genes are not transcribed; the phage genome exists in a repressed state. The phage DNA in this repressed state is called a prophage because it is not a phage but it has the potential to produce phage. In most cases the phage DNA actually integrates into the host chromosome and is replicated along with the host chromosome and passed on to the daughter cells. The cell harboring a prophage is not adversely affected by the presence of the prophage and the lysogenic state may persist indefinitely. The cell harboring a prophage is termed a lysogen."

Thus, the phages of this invention are those termed virulent or non-lysogenic. Unlike other methods for treating biocorrosion in which lysogenic phage are induced by stressing bacteria using, e.g., a UV treatment (see, e.g., WO/20021040642), the present invention makes use of virulent viruses, i.e., those that enter the lytic phase and kill their host bacteria without external stress or inducement to produce their activity. It has been found that such temperate phages (produced by lysogenic host bacteria) are not appropriate for use in biocontrol in their temperate state. The present invention requires no such induction (except in one special embodiment) because it takes advantage of virulent or lytic viruses to deliver, e.g., in a large bolus, an overwhelming amount of lytic virus to shift the balance against the microbial population causing biocorrosion in the local milieu. Bacteriophage produced from stressing lysogenic bacteria and virulent bacteriophage are different in that virulent bacteriophage lack the genetic capacity to form lysogens. The difference, in more detail is explained by the pathways that a phage might follow.

Upon infection of their bacterial host, there are several pathways that a phage might follow, depending on the genetics and physiology of the phage, the genetics and physiology of the host bacteria, and environmental conditions. The most obvious pathway is that of a lytic infection: during a lytic infection the phage genome is replicated, phage proteins are made, and the phage kills and lysis the host bacteria. Another pathway, called a lysogenic pathway, proceeds by the phage forming a stable (or meta-stable) association with the bacterial host, in the form of a prophage. A prophage is a quiescent phage genome either integrated into the host genome or existing as an extrachromosomal element. A bacteria that contains a stable, or meta-stable, phage genome is termed a lysogen. In some cases, a prophage may be induced by stressing the lysogenic host bacteria. An induced prophage proceeds through the phage lytic cycle, resulting in the death of the host bacteria and the release of infective progeny phage into the environment. These phage may go on to infect new hosts, and may enter into lysogenic or lytic cycle. Importantly, a lysogenic bacteria is resistant to superinfection by any phage for which it is a lysogen and infection of a bacterial culture with a temperate phage results in the very rapid recovery of phage-resistant lysogens. A virulent phage lacks the genetic capacity to form lysogens and primarily enter a lytic infection cycle that results in the death of the host and does not result in the rapid development of a phage resistant, lysogenic population. It is for these reasons that the use of virulent phage instead of temperate phage is preferred.

Water-based drilling mud and hydrofracture fluits generally contain various thickeners are used to influence the viscosity of the fluid, e.g. xanthan gum, guar gum, glycol, carboxymethylcellulose, polyanionic cellulose (PAC), or starch. These viscosity additives to "frac" and "flood" water are, ironically, food sources for fouling bacteria. Bacterial degradation of the viscosity additives occurs early in the hydrofracture water tanks and in the subsurface, causing premature viscosity drops and fracture closing. When a panel of phage cocktails is mixed into the hydrofracture fluids, these premature failures may be abated or avoided, forestalling otherwise rapid decline of the wells and retaining production rates. Phage products may also impart a level of immunity to the reservoir, thereby extending the commercial life of a producing well.

In one embodiment of this invention, as more fully detailed below, high concentration virulent phage solution is first injected into a well, followed by the bulk of the "fracing" water, thus enhancing the immunity of the reservoir by filling the fractures with the highest level of virulent phage biocide.

Where the "fracing" is conducted in stages or segments—where a segment of the well is fractured (after perforating if there is casing) and then temporarily sealed—higher concentrations of phages will be injected into each segment as the segment is fractured. High concentration of phages is highly desirable to initiate infection of problematic bacteria.

Other petroleum resources will be similarly positively impacted. Petroleum reservoirs will be prevented from souring during water flood operations, as phage products will kill SRB and impart a persistent level of immunity to the reservoir. Phages can also be used to treat existing reservoirs. Thus, the use of phages in accordance with this invention will reduce completion costs, workovers and re-completions, and, most importantly, overall production costs due to capital and operational expenses associated with bacterial fouling, corrosion control and repairs.

As used herein, the following definitions apply: A phage cocktail includes multiple, receptor independent phages for each target bacterial host. This is different from a phage panel, which is a collection of phages chosen to cover as wide a host range as possible. For the purposes of this invention, the phage treatment of waters will consist of a panel of phage cocktails, that is, there will generally be at least two phage cocktails for each of several target SRB bacteria, and two virulent phages for each target bacteria. Since some SRB phages are known to be polyvalent—effective against more than one strain of SRB—there may not need to be a separate cocktail for every strain of target bacteria. This panel of cocktails is designated herein as phage "multi-panel".

A somewhat typical flow scheme for a "fracing" operation (as, for example, in a Barnett Shale gas well) may be understood by reference to FIG. 1. Water from a lined storage pit 200 is pumped into one of several 500 bbl temporary storage vessels (tanks), 201, 202 and 203, or the tanks are filled directly from other water sources. Water in the storage pit may be tanked in, produced from water well(s), river water, natural run-off water, or any other convenient source. For reference, a half acre pit of 6 ft average depth contains 488,779 gallons. Most of the water sources will be heavily contaminated with bacteria. Since the pit is open it will have additional air-borne and run-off bacterial contamination with numerous and varied bacterial strains.

Water from the temporary storage vessels (tanks) is mixed with chemical additives and proppants, to hold the fractures open (usually sand or ceramic beads), and with biocides from tank 204 (usually a tank truck). Water and additives are mixed in mixer 220 and picked up by high pressure pump(s) 212 for high pressure injection into a wellbore 300. This high pressure water causes fractures or cracks in the gas bearing rock or shale formation allowing the gas to be released to exit the well through the well bore. The proppants help hold the fractures open.

The well bore 300 is sealed up-well of the to-be-fractured area by packer(s), 301, to maintain pressure in the wellbore during "fracing". Water pumping rates range from about 10 bbl/minute to as much as 200 barrels/minute (420-8,400 gal. per min.). Rates of 70-80 barrels/minute are typical in Barnett Shale wells. The "frac" water may be injected in one or more stages, or may be injected into individual segments of the well bore. For example, the segment of deepest portion of the well may be sealed and fractured, then filled with sand and the tools pulled back to seal and fracture a second segment, and so on. For the purposes of this invention, each of these segments may be considered a separate "frac" operation.

After the desired amount of water has been pumped into the well for fracturing, the well sits idle while production equipment is installed at the well head. Thus, the well may sit with "frac" water in it for days or months. During this time bacteria grow and produce acid and sulfur compounds in the reservoir formation. Moreover, these bacterially produced compounds will cause further problems when the water is returned to the surface, including microbially induced corrosion (MIC) of top side equipment.

When the surface production equipment is installed, the injected water is allowed to return ("flowback" and "produced" water) to the surface for disposal, shown in FIG. 1 as stored in tank 206. In "fracing" operations, generally about 20-40% of the injected water remains in the formation. The flowback or "produced" water contains oil, salts, contaminates, and increased bacterial concentrations, but increasingly recycled for environmental reasons. In a study of biocides in several Barnett Shale wells, the bacteria level increased at least one order of magnitude from the source water, e.g. from $1\times10^6$ bacteria/ml to $1\times10^7$ pfu/ml. Increasingly, recycle, and treatment of the "produced" water, is required.

According to this invention, bacterial control is accomplished by adding an effective amount of virulent bacteriophage solution, as in a phage multi-panel, to the "frac" water as, for example, by adding it to the water storage pit (pond) or temporary storage vessels (tanks). In water flood operations, to enhance production, or in an already soured reservoir, the bacteriophages will be added to the water or injected with the water to combat SRB and will prevent further degradation and production of $H_2S$.

If phage multi-panel is added to the "frac" water pond, it is preferred that it be added under the surface of the water (SRB are anaerobic), and added slowly in discrete locations—such as can be accomplished with a soaking hose or similar injection means. If the phage multi-panel is distributed in discrete volumes, rather than by rapid mixing, the phage concentration level remains high in the area immediately surrounding the injection for sufficient time to allow phages to infect target bacteria. The rate at which phages attach to, infect and lyse target bacteria is highly dependent upon the concentration of phages and target bacteria. Generally, it is desired that each be at least about $1\times10^5$ pfu/ml. By slowly seeping the phage multi-panel into the water, the phages form a pocket of high concentration surrounded by concentrated bacteria. As the phages infect and lyse target bacteria, the number of phages multiplies exponentially; thus, the phages diffuse through the water in a kind of wave of concentrated phage attack of the surrounding bacteria. If, on the other hand, the phage multi-panel is rapidly and thoroughly mixed with the "frac" water in large volumes, the concentration is greatly reduced and the phage infection of bacteria is slowed to unacceptable levels. Thus, a means of slowly adding the phage solution, such as a type of "soaking hose", is desirable.

Because the quantity of water is so great, large amounts of bacteriophage solution will be needed if the entire "frac" water is to be treated. Moreover, phages are not mobile—they have no mechanism for moving about to find and attack target bacteria. Phages must be brought into physical contact with target bacteria. Therefore, in one embodiment, the needed virulent phages are generated on-site. This is accomplished in a phage proliferator/concentrator process.

Phage Proliferation and Concentration

In order to produce a sufficient amount of bacteriophages to treat the large volume of water, phages may be replicated and concentrated on site. Fortunately, propagation of virulent phages is achieved by the bacteriophage injecting itself into its matching bacteria and replicating itself at the same time as it destroys the bacteria—as is also explained in more detail below. Bacteriophage proliferation for use in treating the "frac" or "flood" water is illustrated in FIG. 1. In general it is preferred, and sometimes necessary for the entire proliferation/concentration system to be blanketed with a non oxygen gas. Nitrogen is preferred, since the SRB are aerobic and will be killed if there is significant oxygen in the system.

Vessel 101 is a proliferator/concentrator. Water containing target bacteria is pumped into vessel 101 through valve 120, where it is mixed with bacteriophage panel or multi-panel virulent for the target bacterial strains, shown as being pumped out of vessel 104 with pump 110 through valve 124 to be mixed with the incoming bacteria-containing water. Some forms of SRB will be substantially destroyed by their specific virulent phages in less than 20 minutes. The concentrator vessel is sized to provide a flow rate of concentrated bacteriophage solution sufficient to treat the desired volume of "frac" water. A 4 ft diameter vessel will have a volume of 12.6 ft3/ft of height. A 6 ft diameter vessel will have 28.3 ft3/ft. Thus, a 4 ft diameter vessel, 8 ft tall, will contain 100.8 ft3' and a 6 ft diameter vessel, 8 ft tall, will contain 226.4 ft3.

A flow rate of 9.3 gpm in the 4 ft. diameter reactor, and 37.7 gpm in the 6 ft. diameter reactor, will provide 20 minute residence time (equivalent to the time needed for a substantially complete kill of some strains of SRB bacteria). Residence time will, of course, vary with flow rate, and can be suitably adjusted to provide sufficient time for phage replication for each phage species.

Concentration of bacteriophage in solution leaving vessel 101 depends upon the concentration of target bacteria in the incoming water. When matching bacteria are present, some phages may be replicated by a factor of about 20:1. Therefore, for example, when the incoming water contains $2 \times 10^6$ pfu/ml, the outgoing stream will contain $4 \times 10^7$ pfu/ml. If the replication is 100:1, then the outlet stream will have a phage concentration of $1 \times 10^8$ pfu/ml—a two orders of magnitude increase. The phages will continue replicating themselves so long as a sufficient concentration of target bacteria remains in the water. Thus, the replication will continue when the outgoing concentrated phage solution is mixed with bacteria-containing "frac" water.

Initially, the proliferator/concentrator is fed with a solution of bacteriophage multi-panel (mixture of virulent phages) that has been separately generated—shown in vessel 104 and passed to the proliferator/concentrator through valve 124 by pump 110. Once the concentrator is functioning, phages may be supplied by recycle of a portion of the output stream through valve 128. The amount of recycle will preferably be sufficient to provide a phage-to-target-bacteria ratio between 1 to 0.001. In general, 10 the recycle will contain about 20 times the concentration of phages as the concentration of target bacteria in the source water since some SRB phages will replicate themselves in target bacteria about 20:1. Some of the concentrated phage solution may be stored for future use, as in one of the temporary storage tanks, 201, 202, and 203.

In FIG. 1, vessels 102 and 103 are used for culturing target bacteria which may optionally be added to the proliferator/concentrator 101 to increase the concentration of incoming bacteria and, hence, the amount of phages produced. Such supplemental bacteria may also be varied to generate a desired concentration of phages in the output stream. Culturing of bacteria may be conducted on-site or at an off-site, centralized location and brought to the treatment site. Alternatively, target bacteria may be concentrated from the "frac" water or other source in a tangential flow filter system. Such a system is illustrated in FIG. 2.

Figure 2:
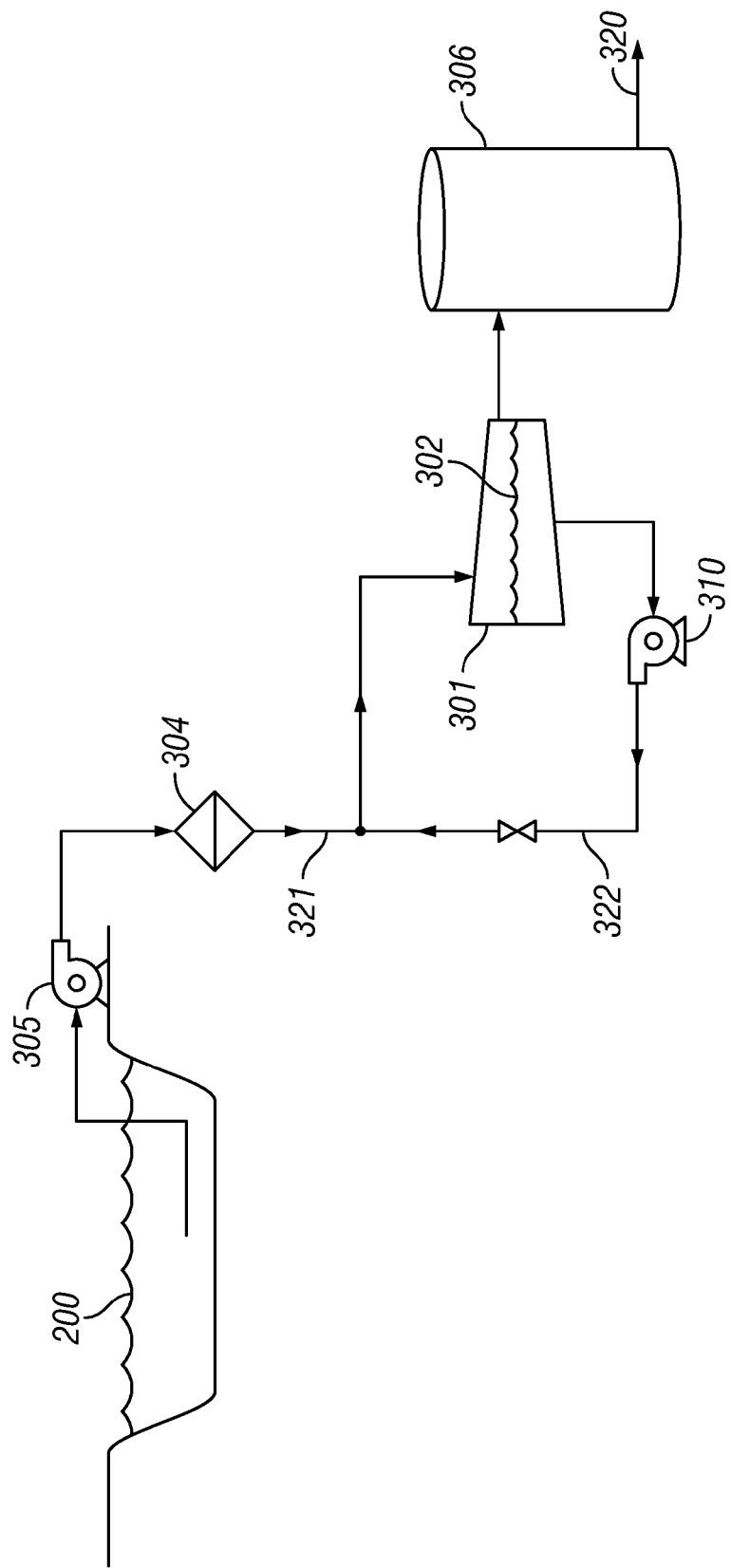
FIG. 2 is a diagrammatic representation of one aspect of a process of the invention.

Referring to FIG. 2, water is pumped from the "frac" water pond 200 (or other suitable storage, as would be required in some water flood operations) by pump 305 to filter 304—a coarse filter to remove larger particles and trash. From filter 304 the water passes by conduit 321 to tangential flow filter 301, having a filter screen, 302, of about 0.2 micron. The screen is sized to hold back SRB and let smaller particles pass. The filter water may be recycled to the filter by pump 310 (through conduit 322). The filtrate passes to tank 306, where it may be directed as needed by conduit 320.

The illustration in FIG. 2 shows the water source as the "frac" water pond. It may, of course, be any suitable source. In one embodiment, the source will be the "produced" water from the well (see vessel 206 in FIG. 1). In general, the "produced" water will contain salt (NaCl) and some target bacteria, which may be halophilic. If it is found that the offending target bacteria are halophilic, and target SRB from the "frac" water does not survive in the salt water environment of the formation, it will be desirable to isolate target halophilic bacteria recovered from the reservoir Such bacteria can also be cultured, as described above, by using a brine culture solution.

In FIG. 1, vessel 101 contains phages virulent against the target or host bacteria used to start the process. It may be replenished from the concentrated outflow of the phage concentrator 101 or from an external source.

Thus, in operation, the phage concentrator will take in "frac" water from one of the storage tanks 201, 202 or 203 through valve 120 or, alternatively, directly from storage pit 200 through valve 125. Concentrated phage solution may pumped to one of the temporary working tanks 201-203 through valve 121, or returned to the water storage pit 200 through valve 126. In either case, the phages will continue replicating if there are sufficient target bacteria present, substantially destroying most of the target bacteria.

In one embodiment, more concentrated phage solution will be first pumped into the well before the bulk of the "frac" water is injected. For example, if the bulk of the treated "frac" water contains $1 \times 10^6$ virulent pfu/ml, the first solution will be about $1 \times 10^7$ to $1 \times 10^{10}$ pfu/ml. This allows the fracture formation to be saturated with a "packet" of high concentration virulent phage solution to mitigate bacterial growth in the well. In general, this first solution will be about 0.01 to 10%, preferably about 0.1 to 5%, of the total "frac" water injected.

All the vessels 101, 102, 103, and 104 are constructed of simple materials. They only need to be sufficiently strong to hold the solutions. Corrosion is not a particular problem, although they should be able to contain oily "flowback" water, which will include salt and chemical additives. It is desirable that they be able to be washed and sterilized with bleach solution. It is also desirable that they be able to be "blanketed" with a non-oxygen gas. Generally, most plastic materials used for tanks and vessels are suitable, including fiberglass, polypropylene, polyvinyl chloride, and polyurethane. Stainless steel will also be suitable. Other commercially available materials will be obvious to those skilled in the art.

Since bacterial growth, and to some extent phage proliferation, is temperature sensitive, there is provided in one embodiment means for heating either the inlet streams to the vessels or heating the contents of the vessels. The streams may be heated by heat exchange, electrical heaters, or any other suitable means known in the art. The contents of the vessels may be heated with electrical or steam heaters or other suitable heating means known in the art.

These vessels are not especially heavy, and the equipment is not extensive; therefore, in one embodiment the proliferation/concentrator equipment—vessels 101, 102, 103, and 104, and associated pumps, valves and piping—are mounted on a movable platform so that they can easily be transported from well site to well site. These can be mounted on skids (that can be lifted onto a truck bed) or on a trailer or truck bed.

In practical water systems found in industrial use, there will be a multiplicity of bacteria, including many species and genus of SRB. As is well known, the growth rate of bacteria is highly influenced by its environment—temperature, pH, salinity, nature of nutrients and other factors well known in the art. In the process of identifying and culturing bacteria for isolation and proliferation of virulent bacteriophage there will be in the cultured bacteria those that thrive in the culture media and at the culture conditions. Thus, there will appear to be accurate identification of target bacteria. However, the conditions of application of the bacteriophage will likely be different and not necessarily conducive to growth of the cultured target bacteria. Moreover, even when the cultured bacteria thrive in the conditions of application and if the bacteriophage control is effective, when the putative target bacterial are killed or reduced, other sub-dominant bacteria are allowed to grow. Thus, it will appear that the bacteriophage treatment loses its effectiveness when, in reality, it is effective but other bacteria (that were less vigorous in competition of the first target bacteria) grow in the absence of competition of the first dominant bacteria. This phenomenon has been observed experimentally by Applicants in treatment of SRB from mixed waters containing a community of SRBs from oil and gas operations. An embodiment to address this effect is in a section hereinafter.

1. Identifying Target Bacteria:

Target bacteria are identified by sampling the source water and/or biofilm. From samples, the target bacteria can be isolated and characterized, to some extent based on what is generally already known about the causes of corrosion and souring. From these samples, virulent bacteriophages are identified for target bacteria and bio-corrosive organisms, i.e. SRB and APB. Sufficient phages are then isolated to effectively lyse the target bacteria, and an effective amount of phage solution is added to the water used for "fracing" a well formation. SRB comprise Desulfovibrionaceae selected from the group consisting of *D. vulgaris, D. desulfuricans* and *D. postgatei*. In yet another aspect, the bio-corrosive organisms comprise Caulobacteriaceae selected from the group consisting of *C. Gallionella* and *Siderophacus*. A wide variety of organisms may be targeted, e.g., archaebacteria, eubacteria, fungi, slime molds, and small, bio-corrosive organisms. The SRB group of bacteria reduces sulfates to sulfides, releasing sulfuric acid and hydrogen sulfide as byproducts which react with iron to form the characteristic black precipitate iron sulfide. Hydrogen sulfide gas is not only extremely toxic and flammable, but it causes souring of the petroleum product, resulting in reduced quality and increased handling cost. The term "SRB" is a phenotypic classification, and several distinct lineages of bacteria are included under this umbrella term. Target bacteria include members of the SRB including, without limitation, members of the delta subgroup of the Proteobacteria, including Desulfobacterales, Desulfovibrionales, and Syntrophobacterales. Also targeted are the APB bacteria that produce acidic metabolites. This specifically includes sulfur-oxidizing bacteria capable of generating sulfuric acid. This includes, without limitation, sulfur bacteria such as Thiobacilli, including *T. thiooxidans* and *T. denitrificans*. Targeted bacteria further may include bacteria populations and isolates, and further includes corrosion-associated iron-oxidizing bacteria. Also included are isolates of the Caulobacteriaceae including members of the genus *Gallionella* and *Siderophacus*.

Still further, bacterial populations may work synergistically with the bio-corrosive bacteria described above. These include members of microbial consortia exhibiting biofilm formation activity. Such biofilms can provide the anaerobic microenvironment required for the growth of corrosion promoting bacteria. As such, the target of phage treatment can include not just the corrosive metabolite producing bacteria, but also any bacteria involved in forming the microenvironment required for corrosion.

Additionally, biofilm producing bacteria involved in the biofouling process are included in the category of targets for phage remediation. Biofilm forming genera of bacteria include *Pseudomonas* or *Vibrio* species isolated in affected containment systems. Bacterial populations responsible for biofilm blockage may also be selected for phage treatment. All bacteria that are to be targeted for phage treatment are part of the selected bacterial subpopulation.

2. Culturing Target Bacterial Strains:

The target bacteria are cultured by means well known in microbiology. Any means of culturing bacteria that promotes growth of the bacterial population are suitable. For example, liquid cultures of *D. vulgaris* can be grown in ATCC medium1249 Modified Baar's medium for sulfate reducers. Plate cultures of *D. vulgaris* are then grown on ATCC medium: 42 *Desulfovibrio* medium. Cultures have been grown at either 22° C. or 30° C. in anaerobic GasPak jars (VWR).*D. vulgaris* growth forms a characteristic black precipitate in media containing ferrous ammonium sulfate, an indicator of sulfate reduction.

Sufficient bacteria can be grown and enriched in a relatively small container. Therefore, it is preferred that the initial culturing of bacteria be conducted on site or in-situ, as for example, as illustrated in FIGS. 1 and 2. Larger quantities, as are needed for large scale production of phages, are preferably grown in a centralized location having the equipment and resources needed. If the target SRB bacteria are halophilic, it will be necessary to adjust the culture by addition of NaCl.

3. Identifying Virulent Phages for Target Bacteria:

The geographic distribution of industrial bacterial contaminations is world-wide and transverses many geographic and geological boundaries. Similarly, the sources of phages for controlling bacterial infestations include any site where bacteria are found and, thus, transverses many geographic and geological boundaries. While existing phage stocks can be screened for activity on target bacteria, new phages can also be isolated from the same site or location where the bacteria pose a problem, such as soils, stagnant waters, indigenous water and the like. As the natural predators of bacteria, populations of bacterial phages are most abundant near abundant sources of their prey. Therefore, the process of identifying phages specific for any bacterial population is to first identify an environmental site where that bacterial type is abundant. This means that there is not one environment that will serve as a source of phages for all target microbes. Instead, the exact environmental sample will vary from host strain to host strain. However, there are general guidelines for identifying the environmental sample most likely to yield desired phages. An ideal sample is marine or freshwater sediment from an environment favorable for the growth of the host bacteria. Specific physiochemical properties of the sediments are important. While the exact parameters will vary from host to host, variables to consider include salinity, temperature, pH, nitrogen or eutrophication, oxygen, and specific organic compounds. An example, which is not intended to be a guideline for all protocols, would be the identification of phages active against a sulfate reducing bacterium (SRB) such as *Desulfovibrio*. Sediments enriched in SRB are characterized by a black anoxic layer and the production of odiferous volatiles such as hydrogen sulfide. These sediments are common in areas experiencing eutrophication in concert with the resulting oxygen depletion. Therefore, a sample likely to possess SRB specific phages will be a black, hydrogen sulfide producing sediment collected from waters rich in organic compounds.

The choice of a sample site for phage isolation is customized to a specific host bacterium. Phage isolation sites may include any body of water (natural or man-made), sediments, or soil samples. Phage isolation sites may also include man-made structures such as the target water source, containment or settling tanks, creeks, and ditches. Within the man-made structures, the sludge-like deposits composed of organic and inorganic sediments that have settled at the bottom of the structures are often the optimal sampling site for isolation. Phages for any given host can be found at the same conditions relative to salinities, temperatures, pH, pressure, nitrogen concentrations, and oxygen levels that are favorable to the growth of the host bacteria. Bacteria vary greatly with regard to carbon source utilization, similarly phages that infect these bacteria can be found in these environments regardless of carbon source being utilized by the bacteria. Similarly, bacteria and phages vary greatly with regard to tolerance and utilization of industrial waste materials such as metals, heavy metals, radioactivity, and toxic chemical wastes including pesticides, antibiotics, and chlorinated hydrocarbons.

As an alternative to identifying samples based on physiochemical properties, molecular tools are used to identify sediments possessing wild populations of bacteria similar to the target bacteria. These methods typically require some level of purification of DNA from the environmental sample, followed by the detection of marker DNA sequences.

The most straightforward of these are polymerase chain reaction (PCR) based technologies that target 16s rDNA sequences. These can be analyzed by methods such as denaturing gradient gel electrophoreses (DGGE) or by DNA sequencing.

4. Isolation of Novel Phages Active Against Target Bacteria:

It is necessary to match collected phages to a target strain of bacteria; matching in the sense of obtaining a phage sample that is specifically virulent (lethal) for the target bacteria strain. Matching is accomplished by identifying the bacteria strain and empirically applying a phage sample until a clearing of the bacteria is obtained. Not all bacteria will be destroyed because a minimum level is required to initiate infection and clearing. It may also be accomplished without ever identifying the bacteria strain by empirically finding a matching virulent phage from collected or stored phage samples. These empirical methods are more research intensive than specifically identifying the bacteria and/or the virulent phages, but are equally effective for the purpose of this invention.

Using criteria discussed above with respect to the individual characteristics of the target bacteria, an appropriate environmental site will be identified from which phages can be isolated. The primary methodology used to isolate these phages is an enrichment method. Sediment, sludge, or soil samples from the environmental site will be mixed with a solution containing salts and peptides. The exact composition of this solution can vary but, in general, will approach the same composition as Lysogeny Broth (commonly referred to as LB media: per Liter—10 g tryptone, 5 g yeast extract, 10 g NaCl).

The ratio of sample to LB will vary, with the goal of producing a thick, turbid sludge. This is shaken for several hours, and a sterile rinsate is produced from it by sequential centrifugations and filtrations to remove solid material greater than 0.2 microns. This is termed a "rinsate" and the rinsate is then supplemented with concentrated fresh bacterial media (which will vary depending on the exact bacterial host being grown). A small amount of the host is then added to the rinsate/media mix and allowed to incubate for one to several days depending on the growth rate of the host. Incubation conditions including shaking, media temperature, and oxygen levels will be those that promote growth of that particular host. After incubation, chloroform will be added to 0.01% and the solution will be sterilized by sequential centrifugation and filtration to remove intact bacterial cells. This solution is termed an "enrichment". Phages in the "enrichment" are assayed for by several different methods including the plaque assay, liquid culture lysis, or visualization by electron microscopy. The final product is an aqueous solution containing phage particles in a weak phosphate buffer with minimal bacterial cellular debris.

5. In-situ Test of Identified Killer Phage Strains:

Matching of the identified phages and target bacteria or biofilm in isolation is critical to the success of the process of this invention and must be validated in "real life" conditions of the environment in which it is to be used. Thus, the matched phages are tested in the water conditions that exist. This is suitably done in a side-stream or aliquot of the water system to be treated. A suitable means for this test, for example in the "frac" water pit, is to pump a stream of the water source into a suitably sized container or side loop for sufficient time to allow it to come to equilibrium with the water source. The identified phages are introduced into the stream (either batch wise or in continuous flow) and tests are made to determine if the population of target bacteria is reduced.

6. Preparing Suitable Quantity of Identified Phage Multi-panel to Treat the Target Water System:

The treatment phage multi-panel consists of a mixture of virulent phages that have been found to "match" target bacteria and biofilm to be treated. Sufficient phage solution must be manufactured to provide an effective amount and concentration to significantly reduce the target bacteria population, or at least to initiate phage proliferation in a system, as described in reference to FIG. 1. For this, phages exhibiting bacteriolytic activity against target bacteria will be selected. Phage multi-panels may include pre-existing phage isolates as well as the de novo isolation of novel phages from samples taken at the water site. Thus, in one embodiment, the step of producing the infective (virulent) phage panel may further include screening and isolating naturally occurring phage active against the selected bacterial population. In another embodiment, it may be unnecessary to screen for phages where the suspect bacterial populations are already known or suspected. Phages may be isolated by a number of methods, including enrichment methods or any technique involving the concentration of phage from environmental or industrial samples followed by screening the concentrate for activity against specific host targets.

Additionally, new methods for isolating phages are likely to be developed, and any phages isolated by these methods are also deemed covered by the claims of this invention. Given the high genetic diversity of phages, these naturally occurring phages will include those with novel genomic sequence as well as those with some percent of similarity to phages known to infect other bacterial clades. Most of the new phages are expected to be members of the taxonomic group Caudovirales, also generally referred to as the tailed phage. The use of phage in an infective cocktail is dependent on the phage's bacteriolytic activity. Bacteria targeted by treatment with phage or phage panels include any isolates present in the target water system.

Phages can be optimized for effectiveness by selection for naturally occurring variants, by mutagenesis and selection for desired traits, or by genetic engineering. Traits that might be optimized or altered include, but are not limited to, traits involved in host range determination, growth characteristics, improving phage production, or improving traits important for the phage delivery processes. Thus, in another aspect, the step of producing the infective phage panel includes creating engineered phages against the selected bacterial population. This will include phages created to have a broad host range. This may be the product of directed genetic engineering, for example.

Collectively, the phages pooled together are referred to herein as the infective phage multi-panel. Initial treatment of a target water system with the infective phage panel is ideally followed up by monitoring the effects of treatment on the selected bacterial subpopulation. Over longer periods of time, it will generally necessary to alter the phage panel to confront bacteria that have developed resistance mechanisms to the infective phage panel. This is especially true if the phages isolated above ground and in the absence of salt are found to not be viable at down-hole formation conditions. Additionally, new bacterial species may begin to thrive in the absence of the initial selected bacterial subpopulation. Thus, the need may arise to alter the infective phage panel over time. New infective phage multi-panels may be created in response to either resistant strains or new bacterial populations causing biofilm fouling or bio-corrosion. The effectiveness of the infective phage panel is, in one embodiment, monitored by evaluating changes in phage and bacterial host populations within the system. One can either determine the presence of such bacterial populations directly, or simply monitor the formation of new biofilms and the reoccurrence of bio-corrosion events.

Large Scale Phage Production

Phages are produced, in one embodiment, using a standard liquid lysate method. It should be noted that industrial scale phage production has been achieved inadvertently by the dairy industry and historically by the acetone/butanol fermentation industry, which demonstrates the feasibility of aerobic and anaerobic phage production on this scale.

1. Prepare an exponentially (=OD600~0.3) growing stock of the target host bacteria in the volume of liquid corresponding to the desired final lysate volume. This is done by inoculating the media from a stationary stage liquid culture to a very low cell density (OD600~0.01) and monitoring growth spectrophotometrically until the desired OD is reached.

2. Inoculate this culture with phage to a moi (multiplicity of infection=ratio of phage particles to individual host cells) of 0.1 to 0.001.

3. The culture is then incubated until lysis is observed; incubation is typically overnight but can take several days depending on the host growth rate. At this point, the lysate is ready for purification of the phage particles away from both bacterial cell debris and the components of the culture media. This is accomplished first by vacuum filtration through a filter series with the final pore size being 0.2 µm. Finally, tangential flow filtration will be used to replace components of the media with 10 mM phosphate buffer and, if necessary, to concentrate the phage.

Since phages are notoriously hardy, they may be concentrated, freeze dried and stored for long periods of time without loss of effectiveness. Phages may also be encapsulated with a coating that dissolves in water. This allows phage panels (cocktails) and multi-panels to be shipped to remote locations for use. It allows the manufacture to be made at optimized central locations. While it is desirable that steps 1-6 be performed "on location," it is sometimes preferred that the manufacture of the large scale phage panel be centralized in locations where the necessary equipment and resources are readily available.

One embodiment the invention is a process for remediation of target bacteria, particularly sulfur reducing bacteria (SRB), in waters having a multiplicity and diverse host target bacteria ("target water"). This is accomplished by employing serial or staged bacteria culturing and lysing of dominant and sub-dominate bacteria. For example, remediation of sulfur reducing bacteria (SRB) is effected by application of a series of bacteriophages isolated from the staged culturing and bacteriophage lysing of successive aliquots of waters containing a multiplicity of SRB.

Control of a broad range of target bacteria is achieved by application of virulent bacteriophage(s) obtained by culturing dominant bacteria in a mix of bacteria by:
  culturing a dominant group of bacteria in a mixed bacteria solution, isolating virulent phage(s) for the dominate bacteria, lysing dominant bacteria from a sample of the mixed bacteria solution to remove the dominant bacteria from the mix;
  culturing the next dominant strain from the solution with the dominate strain lysed, isolating a virulent phage for the next dominate bacteria, lysing it to remove the next dominate bacteria; and continuing the sequence to provide a set of bacteriophage that will lyse the dominate and sub-dominate bacteria; and
  applying an effective amount of the isolated phage(s) to a target solution of mixed bacteria.

This sequencing will provide a basis for production, as disclosed herein, of phage panels that will lyse dominate and sub-dominate bacteria in a mixed community of bacteria. These phages can then be mixed and applied to lyse both dominate and sub-dominate bacteria in any environment. The so isolated bacteriophages for dominate and sub-dominate bacteria can be applies sequentially to lyse first the dominate bacteria(s) and subsequently the series of sub-dominate bacteria(s) that proliferate when the next dominant bacteria is reduced or removed. The staging can be applied in response to tests to determine when the sub-dominate bacteria begin to proliferate in the mixture or simply on a timed schedule. For example, phage virulent for the dominate bacteria is first applied to a mixture of target bacteria and when growth of sub-dominate bacteria are detected phage virulent for the first sub-dominate bacteria are applied and the sequence continued for isolated sub-dominate bacteriophage.

In another embodiment, where temperate phage are produced, temperate phage are isolated by assaying the culture supernatant for the steady-state phages produced, or prophage are induced by application of a stressing agent such as a chemical (for example, mitomycin C) or ultraviolet radiation. Temperate phages may be used directly or a virulent isolate of the temperate phages may be first isolated prior to use in SRB control.

Thus, in this embodiment, phage is isolated for control of a diverse mix of target bacteria by:
  culturing a dominant group of bacteria from a diverse mixture of target bacteria, isolating virulent phage active against the dominant bacteria;
  isolation of temperate phages from these bacterial strains from the culture supernatant;
  stressing the temperate bacteria to convert into virulent phages for use in phage preparations;
  continuing the sequence until a collection of bacteriophage is assembled that will effect significant and lasting of problematic bacteria; and Stressing bacteria containing temperate (or lysogenic) phage to cause temperate phage to lyse and produce phage that will lyse other bacteria is described in patent Application to Illison, WO02/40642, May, 23, 2002. Illson discloses, at page 2, "Stressing bacteria so that they lyse or rupture and die producing viruses called bacteriophages which then kill other bacteria is a very efficient way of killing bacteria without the large scale use of biocidal chemicals which can be damaging to the environment. The bacteriophages produced by the lysing bacteria are specific to other bacteria of the same type.

The bacteria can be stressed by any suitable method such as the application of an appropriate amount of ultra-violet light, heat, antibiotics or chemicals that are toxic to the bacteria. The amount of ultra-violet light, heat, toxic or stress inducing chemicals or antibiotics to which the bacteria are exposed is predetermined in experiments to ensure that it stresses a bacterium but does not immediately kill it before it produces bacteriophages which can then be used to kill other bacteria." The disclosure of WO02/40642 is incorporated herein and made a part of the disclosure of this invention.

Target bacteria will generally be sulfate reducing bacteria (SRB), or acid producing bacteria.

The processes of this invention are particularly suitable for remediation of *Desulfovibrio* species bacteria.

Culturing of SRB from mixed bacteria containing waters, isolating phage virulent for cultured bacteria and reproducing the phage and assembly of phage panel and cocktail are described above and also well described in U.S. Pat. No. 8,241,498 issued Aug. 14, 2012; U.S. Pat. No. 8,168,419 issued May 1, 2012; U.S. Pat. No. 8,252,576 issued Aug. 28, 2012, U.S. Pat. No. 8,252,519 issued Aug. 28, 2012 and Published application US 2009/0180992 published Jul. 16, 2009, the relevant disclosures and figures of which are incorporated herein by reference.

Phage once isolated can be proliferated to production level for use by means known in the art.

Two traits of significance in culturing bacteria are the bacterial growth rate as well as the bacterial concentration. Experiments were conducted in batch cultures. Batch cultures are prepared by inoculating liquid media and allowing the culture to grow without addition of fresh media or removal of spent media. Batch cultures undergo "single step growth kinetics", such that the culture progresses through an initial period of slow growth known as "lag phase", followed by a period of rapid, logarithmic growth known as "log phase", and finally, the culture enters "stationary phase" during which the growth rate slows or even stops as nutrients in the media were depleted and metabolic wastes build up and poison the culture. Log phase is further divided into early, middle, and late log phase. Bacteria with slower doubling times may take days or weeks to accumulate to a high enough level to perform each step of the phage isolation and purification. The time required to conduct efficacy studies also increases as growth rate decreases. The second growth characteristic of each strain that needed to be evaluated in order to conduct phage efficacy trials was the typical concentration of cells, in terms of active cells/ml during the different stages of growth.

The bacterial cells/ml value is needed in order to estimate the multiplicity of infection (MOI) during the efficacy trials. MOI is the ratio of phage particles to bacterial cells added to the experiment. Experiments are typically conducted at MOI of 0.01, 0.1, 1, 10, and 100.

The traditional method used to monitor bacterial growth is by measuring changes in light absorption at $A600$ using a spectrophotometer and correlating this value to the number of colony forming units (cfu) per ml. Several issues prevented this from being accomplished in the traditional method. First, when made with iron sulfate, standard MPB media contains precipitates that interfere with spectrophotometric readings. Therefore, all experiments in which $A600$ are measured were conducted using media in which the iron sulfate is omitted. Second, the SRB do not form colony-forming units quantitatively because growth is less robust on solid media. To accommodate this limitation, instead of colony forming units, the cell concentration at different points in the experiments was determined by MPN or serial dilution analysis The first step in isolating phages active against the SRB was to evaluate the capacity of the different SRB to form confluent lawns in top agar. This step is required to visualize phage plaques following standard procedures. Lawns prepared using *D. longus* and *D. alaskensis* develop in over 48 hours. Lawns prepared using *D. desulfuricans* and *D. gabonensis* lawns were too thin for assaying phage on MPB plates.

Efforts to improve lawn characteristics by increasing the amount of bacteria did not improve lawn characteristics. Phage isolations were performed using the enrichment method. Phage enrichments were set up with purified SRB and ATCC strains using various rinsates, including 3 samples provided from an operating gas well, as well as 22 additional samples (Table 3 and data not shown). Enrichments were set up in 50 ml volumes, containing 25 ml fresh MPB, 25 ml environmental rinsate, and 0.2 ml of log phase host cells. The enrichments were incubated at room temperature and sampled for the presence of phage at 1, 3, 7 and 14 days. At each time point, phages were screened by spotting filter-purified enrichment onto lawns of each host.

In samples where phages were detected, the highest concentrations of phage were observed 3 days into the enrichment, after which titers begins to drop. Phage present in positive enrichments was processed by plaque purification. To accomplish this, phage were diluted and plated in overlays. Well-separated plaques were excised and phage eluted, forming a pickate. The pickate was then diluted and plated in an overlay lawn and the pickate process repeated. Finally, the phage stock was amplified in a stepwise fashion, first by making a 5 ml lysate from a single plate and then generating a 50 ml phage stock. The SRB phage titers were typically found to be quite low, typically between $10^6$ to $10^8$ pfu/ml. In contrast, a typical *E. coli* phage stock will have a titer of approximately $10^9$ pfu/ml.

Since bacteria growth and survival (and dominance) are influenced by indigenous conditions, such as temperature, salinity and pH of the water and the like, it is preferred that culturing as described above is conducted under conditions that simulate those where use of the produced phage panel/cocktail will be made. Simulating such conditions present some special problems in culturing and testing of isolated virulent phage.

The invention is generally described herein in relation to SRB in oil and gas well water applications. But the invention is equally applicable to other SRB containing waters such as cooling tower water, pulp and paper mill waters, and the like such as waters described in U.S. Pat. No. 8,241,498, Aug. 14, 201, the relevant disclosures of which are incorporated herein by reference.

Culturing at Approximated Anaerobic Treatment Conditions and Elevated Temperature.

The subsurface environment varies from ambient temperature and pressure to extremely elevated temperatures and pressures considered non-permissive for life. Organisms that require elevated temperatures and pressure require special manipulation. High temperature conditions complicate almost every step in the phage isolation and manipulation process. For example, standard phage agar solidifies at around 50° C., however, bacteria such as *Archaeoglobus* is likely to require at least 70° C. for regular growth. Therefore, visualizing plaques in culture overlays require the use of high-temperature solidifying agents, for example the use of gellan gum based solidifying agents, sold under the trade name of Phytagel (Sigma) (Wirth et al., 2011).

Experimental Evidence

In sample waters of test oil well site (produced water) *Desulfovibrio* species were found to be present at all sites at well site and the only SRB at most sites. *Desulfovibrio* species from the site were found to be closely related to cultured *Desulfovibrio* species. Examples of different SRB established in mixed cultures from the site included strains highly similar to the following database entries: *D. vietnamensis* (T) type, strain: G3 100 ID95-371; (X93994), *D. desulfuricans desulfuricans* Essex 6, ATCC29577 (AF192153), *D. alaskensis* (T) type strain: Al1=NCIMB 13491, (Y11984) as well as *D. dechloracetivorans* Mic 13c06 (AB546251) (Magot et al., 1992; Tardy-Jacquenod et al., 1996; Feio et al., 1998; Motamedi and Pedersen, 1998; Sun et al., 2000; Allen et al., 2008).

Mixed cultures with combinations of the ATCC strains as well as de novo produced water SRB isolates were established. Phage were isolated that exhibited activity against each of these strains. Experiments were conducted using these bacterial hosts as either pure or mixed culture treated with single phages.

Figure 3:
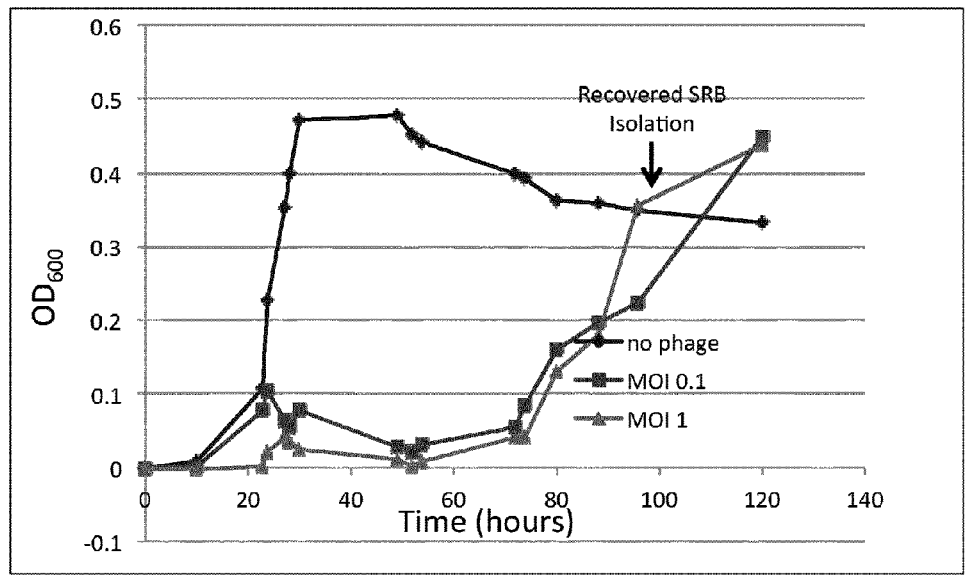
FIG. 3 is a graphical representation of experimental data.

When phage active against only the most abundant member of a mixed bacterial population were applied to the mixed culture, bacterial levels were significantly suppressed for several days (FIG. 3). However, additional incubation time allowed for the bacterial levels to recover.

FIG. 3 describes sequential phage efficacy trials and isolation of phage that overcome culture recovery. It is a growth curve of host Dala14563 either alone (no phage, diamonds) or treated at time zero with phage phiDalaCJ1 at MOI of 0.1 (box), or 1 (triangle). At the indicated time point, the SRB growing in the MOI=1 sample was isolated. Sequence analysis indicated that the recovered host is a resistant derivative of the input host.

Figure 4:
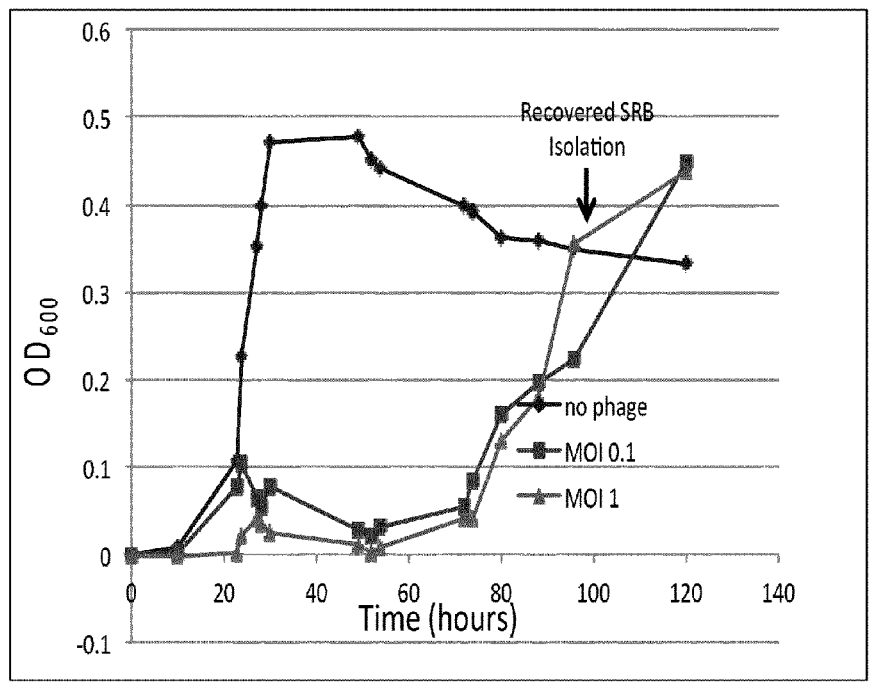
FIG. 4 is a graphical representation of experimental data

Two mechanisms were found to be responsible for the recovery. In some cases, phage resistant representatives of the dominant bacterial strain applied to the experiment arose and proliferated (FIG. 4). FIG. 4 is a growth curve of mixed hosts DalaP4 and DalaP42, inoculated at a >1000:1 ratio, either alone (no phage, green diamond) or treated at time zero with phage phiDalaP4 at MOI of 0.1 (red box), or 1 (blue triangle). At the indicated time point, the SRB growing in the MOI=1 sample was isolated. Sequence analysis indicated that the recovered host is DalaP42, the minority inoculum.

In other cases, the minority organism in the inoculation proliferated and became the numerically dominant organism in the culture (FIG. 4). In both cases, phage capable of killing the bacteria in the recovered population was isolated. This clearly demonstrates that phages can be isolated capable of killing the bacteria that arise following treatment with a partially effective phage preparation.

In another embodiment the invention is a composition that results from:
culturing a dominant group of bacteria in a mixed bacteria solution, isolating virulent phage(s) for the dominate a bacteria, lysing dominant bacteria from a sample of the mixed bacteria solution to remove the dominant bacteria from the mix;
culturing the next dominant strain from the solution with the dominate strain lysed, isolating a virulent phage for the next dominate bacteria, lysing it to remove the next dominate bacteria; and continuing the sequence to provide a set of bacteriophage that will lyse the dominate and sub-dominate bacteria.

A preferred composition will have at least three sequences are conducted to produce a bacteriophage virulent for dominate, sub-dominate and sub-sub-dominate bacteria and one in which the predominant bacteria(s) in the mixed of bacteria solution are sulfate reducing bacteria of the species *Desulfovibrios*.

In this specification, the invention has been described with reference to specific embodiments. It will, however, be evident that various modifications and changes can be made thereto without departing from the broader spirit and scope of the invention as set forth in the appended claims. The specification is, accordingly, to be regarded in an illustrative rather than a restrictive sense. Therefore, the scope of the invention should be limited only by the appended claims.

The invention claimed is:

1. A process for remediation of souring of oil, gas and coalbed geological reservoirs comprising adding to the water used in a hydrofracturing or flooding operation an effective amount of virulent bacteriophage derived from non-lysogenic bacteria and specific for target bacteria, the target bacteria comprising acid producing bacteria and sulfate reducing bacteria.

2. The process of claim 1 wherein the virulent bacteriophage comprises a multi-panel of virulent bacteriophages, each having at least two bacteriophages virulent for each species of target bacteria.

3. The process of claim 1 wherein the effective amount of bacteriophage comprise bacteriophage indigenous to the general location where it is to be applied to remediate reservoir souring.

4. The process of claim 1 wherein a solution of bacteriophage has a concentration of bacteriophage of about $1 \times 10^7$ to $1 \times 10^{10}$ pfu/ml.

5. The process of claim 1 wherein target bacteria comprise sulfate reducing bacteria, sulfuroxidizing bacteria capable of generating sulfuric acid, and iron-oxidizing bacteria.

6. The process of claim 1 comprising:
providing a water pond or storage tank,
adding a solution of bacteriophages virulent for target bacteria to the pond or storage tank solution to at least $1 \times 10^5$ pfu/ml, and
injecting an effective amount of the resulting solution into the reservoir.

7. The process of claim 6 wherein the target bacteria comprise sulfur reducing bacteria.

* * * * *